US009695173B2

(12) United States Patent
Reiter et al.

(10) Patent No.: US 9,695,173 B2
(45) Date of Patent: Jul. 4, 2017

(54) PHARMACEUTICAL COMPOSITIONS FOR THE TREATMENT OF CAPILLARY ARTERIOPATHY

(75) Inventors: Rudolf Reiter, Appenzell (CH); Johannes Tack, Berlin (DE); Reinhard Horowski, Berlin (DE)

(73) Assignee: SINOXA PHARMA GMBH, Berlin (DE)

( * ) Notice: Subject to any disclaimer, the term of this patent is extended or adjusted under 35 U.S.C. 154(b) by 0 days.

(21) Appl. No.: 13/354,832

(22) Filed: Jan. 20, 2012

(65) Prior Publication Data
US 2014/0045879 A1 Feb. 13, 2014

Related U.S. Application Data

(63) Continuation of application No. 12/515,966, filed as application No. PCT/EP2007/010360 on Nov. 23, 2007, now abandoned.

(30) Foreign Application Priority Data

Nov. 23, 2006 (EP) .................................. 060024308
Dec. 6, 2006 (EP) ................................. 0600225263

(51) Int. Cl.
*A61K 31/519* (2006.01)
*C07D 471/06* (2006.01)
*A61K 31/00* (2006.01)
*A61K 31/48* (2006.01)

(52) U.S. Cl.
CPC ............ *C07D 471/06* (2013.01); *A61K 31/00* (2013.01); *A61K 31/48* (2013.01)

(58) Field of Classification Search
None
See application file for complete search history.

(56) References Cited

U.S. PATENT DOCUMENTS

| 4,593,032 | A | 6/1986 | Kehr et al. ..................... 514/288 |
| 8,580,801 | B2 * | 11/2013 | Henkin ..................... 514/263.34 |
| 2002/0122773 | A1* | 9/2002 | Pairet et al. ..................... 424/45 |
| 2004/0247628 | A1* | 12/2004 | Lintz et al. ..................... 424/400 |
| 2006/0105030 | A1* | 5/2006 | Windt-Hanke et al. ...... 424/449 |
| 2009/0264461 | A1* | 10/2009 | Monnier et al. .............. 514/305 |

FOREIGN PATENT DOCUMENTS

| DE | 4240798 | 6/1993 | ........... H01R 43/048 |
| GB | 2192541 | 1/1988 | ............. A61K 31/48 |
| WO | WO 02094238 | 11/2002 | ................ A61K 9/72 |
| WO | WO 2005049088 | 6/2005 | ............. A61K 45/06 |

OTHER PUBLICATIONS

Schwerzmann, M. et al. Atrial septal defect closure in a patient with "irreversible" pulmonary hypertensive arteriopathy. International Journal of Cardiology. 2006, vol. 110, pp. 104-107.*
U.S. Appl. No. 13/885,058, filed May 2013, Horowski et al.*
Robbins Pathologic basis of disease, RS Contran, V Kumar, SL Robbins—Philadelphia: WB Saunders, 5th ed., 1994.*
Jeffery et al., Molecular and cellular basis of pulmonary vascular remodeling in pulmonary hypertension, Progress in Cardiovascular Diseases, vol. 45, Issue 3, Nov.-Dec. 2002, pp. 173-202.*
Wright et al., Thorax 2005; 60: 605-609.*
Cejka, Jan, et al. "Structural Study of Dopamine Agonist Lisuride", Collect, Czech. Chem. Commun.; 2003, 2150-2158, vol. 68.
Husak, Michal, et al., "Crystal forms of Semisyntheitc Ergot Alkaloid terguride", Collect. Czech. Chem. Commun.; 2002, 479-489, vol. 67.
Husak, Michal, et al., "A Conformational Study of the Semisynthetic Ergot Alkaloid—Terguride", Collect. Czech. Chem. Commun., 1003, 2944-2954, vol. 58.
Kratochvil, Bohumil, et al., "X-Ray Structural Study of Terguride Solvates-Terguride Methanol Solvate", Collect.Czech. Chem. Commun., 1994, 149-158, vol. 59.
Kratochvil, B, et al., "The Crystal and Molecular Structure of Terguride Monohydrate", Zeitschrift fur Kristallographie, 1993, 77-86, vol. 206.
Luquin, M.R. et al., "Parenteral Administration of Lisuride in Parkinsons's Disease", Advances in Neurology, 1986, 561-568, vol. 45.
Obeso, J.A. et al., "Intravenous Lisuride Corrects Oscillations of Motor Performance in Parkinson's Disease", Ann Neurol., 1986, 31-35, vol. 19.
Setola, et al., "3,4-Methylenedioxymethamphetamine (MDMA, "Ecstasy") Induces Fenfluramine-Like Proliferative Actions on Human Cardiac Valvular Interstitial Cells in Vitro", Molecular Pharmacology, vol. 63, No. 6, Jun. 2003, pp. 1223-1229.
Jahnichen et al., "Agonism at 5-HT2B receptors is not a class effect of the ergolines", European Journal of Pharmacology, vol. 513, Apr. 2005, pp. 225-228.
Reilly, et al., "Raynaud Phenomenon: Whether it's primary or secondary, there is not cure, but treatment can alleviate symptoms", AJN, Aug. 2005, vol. 105, No. 8, pp. 56-65.
Hachulla et al., "Sclerodermie systemique", EMC-Rhumatolgie Orthopedie, vol. 2, 2005, pp. 479-500.
International Search Report for corresponding PCT/EP2007/10360 mailed Apr. 1, 2008, three pages.
Office Action sent Jul. 21, 2011 in parent application, U.S. Appl. No. 12/515,966.
Bataller, Ramon et al., "Liver fibrosis", Science in medicine, The Journal of Clinical Investigation, vol. 115, No. 2, Feb. 2005, pp. 209-218.
Fabre, A. et al., "Modulation of bleomycin-induced lung fibrosis by serotonin receptor antagonists in mice", European Respiratory Journal, 2008; vol. 32, No. 2, pp. 426-436.
Su, Tung-Hung et al., "Molecular Mechanism and Treatment of Viral Hepatitis-Related Liver Fibrosis", Int. J. Mol. Sci. 2014, 15, pp. 10578-10604.
Zandman-Goddard, Gisele et al., "New therapeutic strategies for systemic sclerosis—a critical analysis of the literature", Clinical & Developmental Immunology, Sep. 2005; 12(3): pp. 165-173.

* cited by examiner

*Primary Examiner* — Svetlana M Ivanova
(74) *Attorney, Agent, or Firm* — Millen White Zelano and Branigan, PC; Csaba Henter; Anthony Zelano

(57) ABSTRACT

The present invention relates to the use of ergot derivatives or ergolines, and in particular of lisuride and terguride for the prophylaxis and treatment of constrictive capillary arteriopathy. Constrictive capillary arteriopathy refers to the diseases pulmonary arterial hypertension, endogenously induced or exogenously induced glomerulosclerosis as well as secondary Raynaud's syndrome.

11 Claims, 2 Drawing Sheets

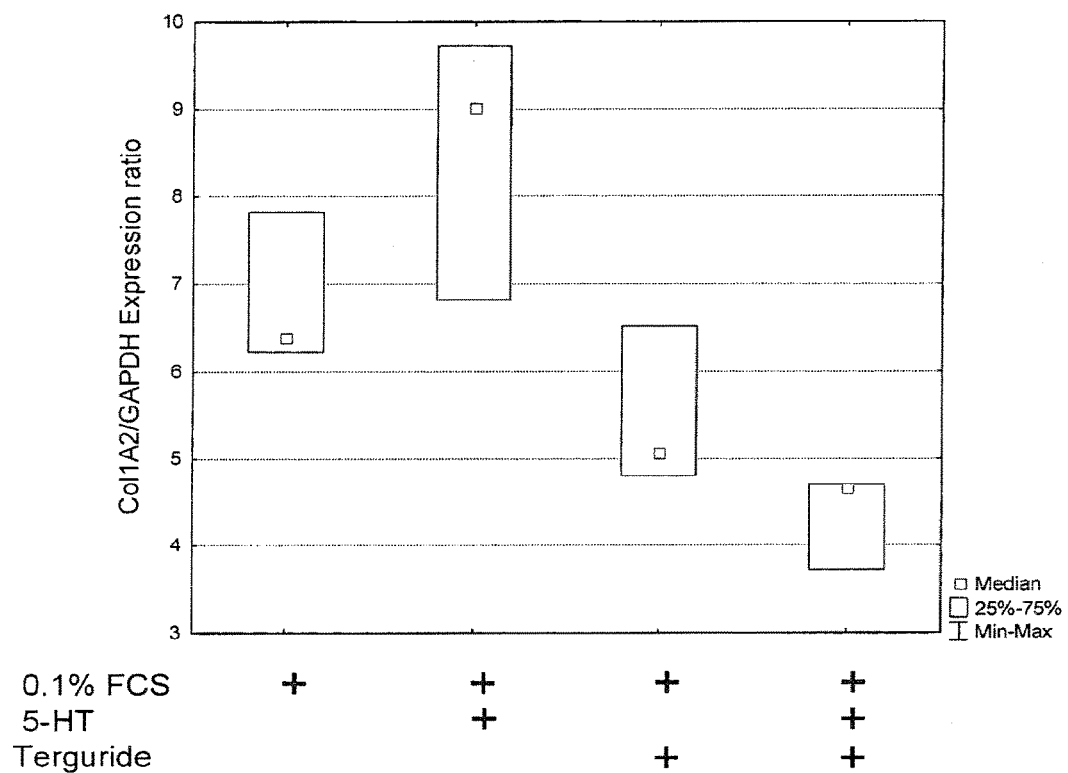
Figur 4

PHARMACEUTICAL COMPOSITIONS FOR THE TREATMENT OF CAPILLARY ARTERIOPATHY

This application is a continuation of U.S. patent application Ser. No. 12/515,966, filed Aug. 3, 2009, which is a 371 of International Patent Application No. PCT/EP2007/010360, filed Nov. 23, 2007, and which claims the benefit of European Patent Application Nos. 20060024308, filed Nov. 23, 2006, and 200600225263, filed Dec. 6, 2006.

SEQUENCE LISTING

The instant application contains a Sequence Listing which has been submitted in ASCII format via EFS-Web and is hereby incorporated by reference in its entirety. Said ASCII copy, created on Sep. 20, 2013, is named BOEHMERP-0118-C01_SL.txt and is 1,385 bytes in size.

The present invention relates to the use of ergot derivatives or ergolines, and in particular of lisuride and terguride for the prophylaxis and treatment of constrictive capillary arteriopathy. Constrictive capillary arteriopathy refers to the diseases pulmonary arterial hypertension, endogenously induced or exogenously induced glomerulosclerosis as well as secondary Raynaud's syndrome or phenomenon.

Constrictive capillary arteriopathy is a pathological characteristic in human medicine for diffuse constrictive arterial lesions comprising a reconfiguration of the vessel walls leading to irreversible stenoses to the point blockages of arterioles. An increase of capillary pressure and an increased vascular resistance can be observed as functional consequences.

Constrictive capillary arteriopathy of various aetiology is manifested in the capillary bed of many types of tissue. The present invention, within the context of capillary arteriopathy, focuses on organ-specific changes that lead to an increase of long-term arteriole pressure and are characterized by the increase of vascular resistance, aggrevative vasospasm and precipitating structural blockage. Thus, the term "capillary arteriopathy" and in particular "constrictive capillary arteriopathy" as used herein denotes the indications glomerulosclerosis and secondary Raynaud's phenomenon and/or syndrome.

It is the object of the present invention to provide further uses of ergot derivatives and in particular of lisuride and terguride.

The object is achieved by the indications described in patent claim 1. Other advantageous embodiments result from the dependent claims, the examples and the description.

It was found, surprisingly, that ergot derivatives and ergolines, and in particular lisuride and terguride are suitable for the prophylaxis and treatment of (constrictive) capillary arteriopathy.

Thus, the present invention relates to the use of compounds having the general formula (I),

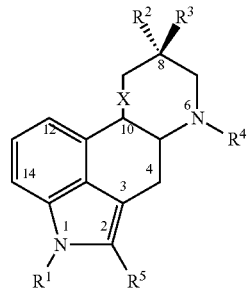

wherein
$R^1$ and $R^4$, independently of each other represent —H, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NH$_2$, —NHCH$_3$, —NHC$_2$H$_5$, —NHC$_3$HT, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_3$, —C$_2$H$_5$, —C$_3$H$_7$, —CH(CH$_3$)$_2$, —C(CH$_3$)$_3$, —C$_4$H$_9$, —CH$_2$—CH(CH$_3$)$_2$, —CH(CH$_3$)—C$_2$H$_5$, —C$_5$H$_{11}$, —C$_6$H$_{13}$, —C$_7$H$_{15}$, —C$_8$H$_{17}$, -cyclo-C$_3$H$_5$, -cyclo-C$_4$H$_7$, -cyclo-C$_5$H$_9$, -cyclo-C$_6$H$_{11}$, -Ph, —CH$_2$-Ph, —CPh$_3$, —CH═CH$_2$, —CH$_2$—CH═CH$_2$, —C(CH$_3$)═CH$_2$, —CH═CH—CH$_3$, —C$_2$H$_4$—CH═CH$_2$, —CH═C(CH$_3$)$_2$, —C≡CH, —C≡C—CH$_3$, —CH$_2$—C≡CH;

$R^2$ and $R^3$ independently of each other represent —$R^6$, —$R^7$, a linear or branched, saturated or unsaturated alkyl residue with 1-10 carbon atoms that can be substituted with one or more of the residues $R^8$-$R^{43}$; a linear or branched, saturated or unsaturated —CO-alkyl residue with 1-10 carbon atoms that can be substituted with one or more of the residues $R^8$-$R^{43}$; a linear or branched, saturated or unsaturated —NH—CO-alkyl residue with 1-10 carbon atoms that can be substituted with one or more of the residues $R^8$-$R^{43}$; a linear or branched, saturated or unsaturated —NH—CO—NH alkyl residue or —NH—CO—N (dialkyl residue) with alkyl residued with 1-10 carbon atoms that can be substituted with one or more of the residues $R^8$-$R^{43}$; an aryl residue or cycloalkyl residue or a dicyclic or tricyclic carbocyclic compound that can be substituted with one or more of the residues $R^8$-$R^{43}$; a heteroaryl residue or heterocyclyl residue or a dicyclic or tricyclic saturated or unsaturated heterocyclic compound that can be substituted with one or more of the residues $R^8$-$R^{43}$;

$R^5$ represent one of the residues —H, —F, —Cl, —Br, —I, —CN or —NO$_2$;

$R^6$-$R^{43}$ independently from each other represent —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NH$_2$, —NHCH$_3$, —NHC$_2$H$_5$, —NHC$_3$H$_7$, —NH-cyclo-$C_3H_5$, —NHCH$(CH_3)_2$, —NHC$(CH_3)_3$, —N$(CH_3)_2$, —N$(C_2H_5)_2$, —N$(C_3H_7)_2$, —N(cyclo-$C_3H_5)_2$, —N[CH$(CH_3)_2]_2$, —N[C$(CH_3)_3]_2$, —SOCH$_3$, —SOC$_2H_5$, —SOC$_3H_7$, —SO-cyclo-$C_3H_5$, —SOCH$(CH_3)_2$, —SOC$(CH_3)_3$, —SO$_2$CH$_3$, —SO$_2$C$_2$H$_5$, —SO$_2$C$_3$H$_7$, —SO$_2$-cyclo-$C_3H_5$, —SO$_2$CH$(CH_3)_2$, —SO$_2$C$(CH_3)_3$, —SO$_3$H, —SO$_3$CH$_3$, —SO$_3$C$_2$H$_5$, —SO$_3$C$_3$H$_7$, —SO$_3$-cyclo-$C_3H_5$, —SO$_3$CH$(CH_3)_2$, —SO$_3$C$(CH_3)_3$, —OCF$_3$, —OC$_2$F$_5$, —O—COOCH$_3$, —O—COOC$_2$H$_5$, —O—COOC$_3$H$_7$, —O—COO-cyclo-$C_3H_5$, —O—COOCH$(CH_3)_2$, —O—COOC$(CH_3)_3$, —NH—CO—NH$_2$, —NH—CO—NHCH$_3$, —NH—CO—NHC$_2$H$_5$, —NH—CO—NHC$_3$H$_7$, —NH—CO—NH-cyclo-$C_3H_5$, —NH—CO—NH[CH$(CH_3)_2$], —NH—CO—NH[C$(CH_3)_3$], —NH—CO—N$(CH_3)_2$, —NH—CO—N$(C_2H_5)_2$, —NH—CO—N$(C_3H_7)_2$, —NH—CO—N(cyclo-$C_3H_5)_2$, —NH—CO—N[CH$(CH_3)_2]_2$, —NH—CO—N[C$(CH_3)_3]_2$, —NH—CS—NH$_2$, —NH—CS—NHCH$_3$, —NH—CS—NHC$_2$H$_5$, —NH—CS—NHC$_3$H$_7$, —NH—CS—NH-cyclo-$C_3H_5$, —NH—CS—NH[CH$(CH_3)_2$], —NH—CS—NH[C$(CH_3)_3$], —NH—CS—N$(CH_3)_2$, —NH—CS—N$(C_2H_5)_2$, —NH—CS—N$(C_3H_7)_2$, —NH—CS—N(cyclo-$C_3H_5)_2$, —NH—CS—N[CH$(CH_3)_2]_2$, —NH—CS—N[C$(CH_3)_3]_2$, —NH—C(=NH)—NH$_2$, —NH—C(=NH)—NHCH$_3$, —NH—C(=NH)—NHC$_2$H$_5$, —NH—C(=NH)—NHC$_3$H$_7$, —NH—C(=NH)—NH-cyclo-$C_3H_5$, —NH—C(=NH)—NH[CH$(CH_3)_2$], —NH—C(=NH)—NH[C$(CH_3)_3$], —NH—C(=NH)—N$(CH_3)_2$, —NH—C(=NH)—N$(C_2H_5)_2$, —NH—C(=NH)—N$(C_3H_7)_2$, —NH—C(=NH)—N(cyclo-$C_3H_5)_2$, —NH—C(=NH)—N[CH$(CH_3)_2]_2$, —NH—C(=NH)—N[C$(CH_3)_3]_2$, —O—CO—NH$_2$, —O—CO—NHCH$_3$, —O—CO—NHC$_2$H$_5$, —O—CO—NHC$_3$H$_7$, —O—CO—NH-cyclo-$C_3H_5$, —O—CO—NH[CH$(CH_3)_2$], —O—CO—NH[C$(CH_3)_3$], —O—CO—N$(CH_3)_2$, —O—CO—N$(C_2H_5)_2$, —O—CO—N$(C_3H_7)_2$, —O—CO—N(cyclo-$C_3H_5)_2$, —O—CO—N[CH$(CH_3)_2]_2$, —O—CO—N[C$(CH_3)_3]_2$, —O—CO—OCH$_3$, —O—CO—OC$_2$H$_5$, —O—CO—OC$_3$H$_7$, —O—CO—O-cyclo-$C_3H_5$, —O—CO—OCH$(CH_3)_2$, —O—CO—OC$(CH_3)_3$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_3$, —C$_2$H$_5$, —C$_3$H$_7$, —CH$(CH_3)_2$, —C$(CH_3)_3$, —C$_4$H$_9$, —CH$_2$—CH$(CH_3)_2$, —CH$(CH_3)$—C$_2$H$_5$, —C$_5$H$_{11}$, —C$_6$H$_{13}$, —C$_7$H$_{15}$, —C$_8$H$_{17}$, -cyclo-$C_3H_5$, -cyclo-$C_4H_7$, -cyclo-$C_5H_9$, -cyclo-$C_6H_{11}$, -Ph, —CH$_2$-Ph, —CPh$_3$, —CH=CH$_2$, —CH$_2$—CH=CH$_2$, —C$(CH_3)$=CH$_2$, —CH=CH—CH$_3$, —C$_2$H$_4$—CH=CH$_2$, —CH=C$(CH_3)_2$, —C≡CH, —C≡C—CH$_3$, —CH$_2$—C≡CH;

X represents a single bond or double bond;
n represents a whole number from 1 to 10; and to salts, enantiomers, mixtures of enantiomers, diastereomers, mixtures of diastereomers, hydrates, solvates and reacemates of the aforementioned compositions for the preparation of a pharmaceutical composition for the treatment and prophylaxis of constrictive capillary arteriopathy, i.e. of pulmonary arterial hypertension, endogenously induced or exogenously induced glomerulosclerosis and secondary Raynaud's syndrome.

The compounds of the general formula (I) are alkaline, and acid addition salts can be obtained by adding organic or inorganic acids. Acids forming an acid addition salt of the compound of Formula (I) include the following sulfuric acid, sulfonic acid, phosphoric acid, nitric acid, nitrous acid, perchloric acid, hydrobromic acid, hydrochloric acid, methanoic acid, acetic acid, propionic acid, succinic acid, oxalic acid, gluconic acid (glyconic acid, dextronic acid), lactic acid, malic acid, tartaric acid, tartronic acid (hydroxymalonic acid, hydroxy propanedioic acid), fumaric acid, citric acid, ascorbic acid, maleic acid, malonic acid, hydroxymaleic acid, pyruvic acid, phenylacetic acid, (o-, m-, p-) toluic acid, benzoic acid, p-aminobenzoic acid, p-hydroxybenzoic acid, salicylic acid, p-aminosalicylic acid, methanesulfonic acid, ethanesulfonic acid, hydroxyethanesulfonic acid, ethylenesulfonic acid, p-toluenesulfonic acid, naphthylsulfonic acid, naphthylaminesulfonic acid, sulfanilic acid, camphorsulfonic acid, quinic acid (quinine acid), o-methylmandelic acid, hydrogen benzenesulfonic acid, pikric acid (2,4,6-trinitrophenol), adipic acid, d-o-tolyl tartaric acid, amino acids such as methionine, tryptophane, arginine and in particular acid amino acids such as glutamic acid or aspartic acid.

If acid groups are present, base addition salts can also be formed, e.g. alkali metal salts as well as salts with amines. Thus, alkali metal salts such as the sodium salt, the potassium salt, the lithium salt or the magnesium salt, the calcium salt, alkylamino salt or amino acid salts can be formed, for example, with alkaline amino acids such as lysine.

The general formular (I) also comprises stereoisomers, enantiomers, mixtures of enantiomers, diastereomers, and mixtures of diastereomers, with chiral compounds of the following formulae (II)-(IIE) being preferred:

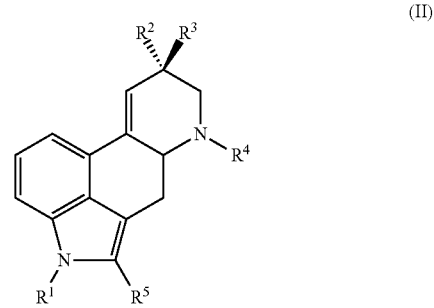

(II)

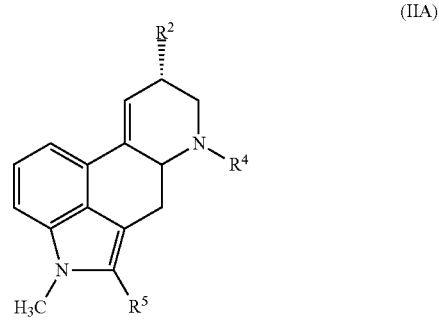

(IIA)

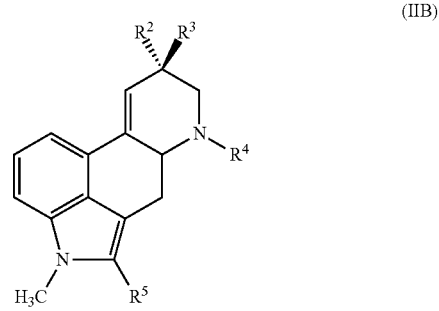

(IIB)

(IIC) 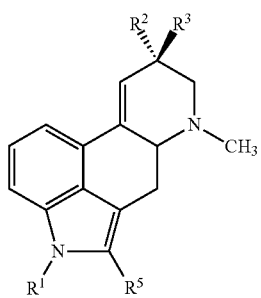

(IID) 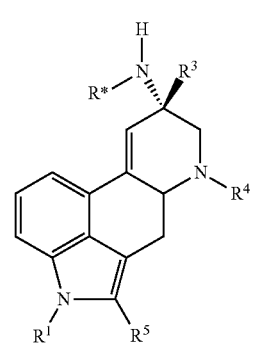

(IIE) 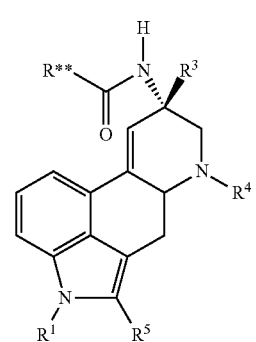

It is furthermore preferred if $R^3$ represents hydrogen. It is furthermore preferred in all formulae disclosed herein if $R^3$ has the configuration shown in the formulae (II), (IIA) and (IIB), that is, that it projects from the plane and that, accordingly, $R^2$ lies behind the plane. Thus, 8-α-ergolines are preferred. In the case where X represents a single bond, the trans position of the two hydrogen atoms at C-5 and C-10 is preferred, as illustrated in the general formulae (III)-(IIIE).

(III) 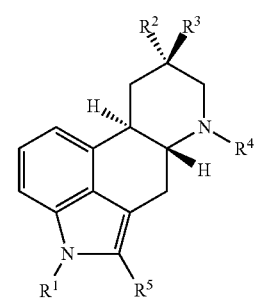

(IIIA) 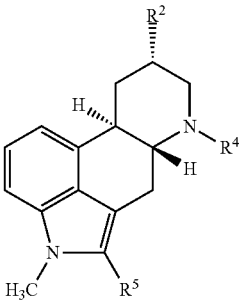

(IIIB) 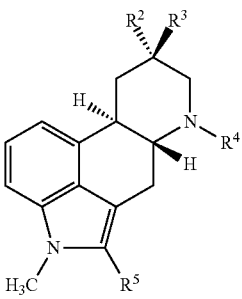

(IIIC) 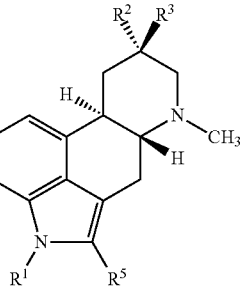

(IIID) 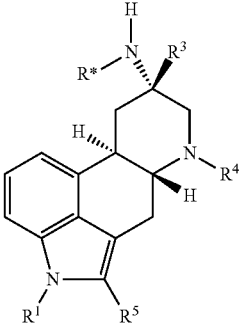

(IIIE) 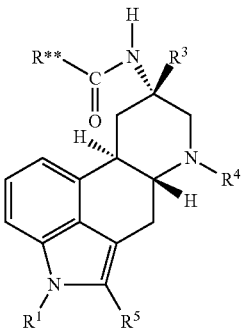

wherein the residues $R^1$-$R^{43}$ have the meaning specified above.

$R^1$ and/or $R^4$ preferably represent hydrogen or an alkyl residue with 1 to 8 carbon atoms. $R^3$ preferably represents a carbonyl group to which a monocyclic, dicyclic or tricyclic heterocycle is bonded.

Moreover, it is preferred if $R^2$ represents a residue —NH—CO—NH$_2$, —NH—CO—NHCH$_3$, —NH—CO—NHC$_2$H$_5$, —NH—CO—NHC$_3$H$_7$, —NH—CO—NH-cyclo-C$_3$H$_5$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—N(C$_3$H$_7$)$_2$, —NH—CO—N(cyclo-C$_3$H$_5$)$_2$, —NH—CO—N[CH(CH$_3$)$_2$]$_2$, —NH—CO—N[C(CH$_3$)$_3$]$_2$, —NH—CS—NH$_2$, —NH—CS—NHCH$_3$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(CH$_3$)$_2$, —NH—CS—N(C$_2$H$_5$)$_2$, —NH—CS—N(C$_3$H$_7$)$_2$, —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—C(=NH)—NHC$_3$H$_7$, —NH—C(=NH)—NH-cyclo-C$_3$H$_5$, —NH—C(=NH)—NH[CH(CH$_3$)$_2$], —NH—C(=NH)—NH[C(CH$_3$)$_3$], —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —NH—C(=NH)—N[CH(CH$_3$)$_2$]$_2$ or —NH—C(=NH)—N[C(CH$_3$)$_3$]$_2$ and in particular a residue —NH—CO—N(CH$_3$)$_2$, —NH—CO—N(C$_2$H$_5$)$_2$, —NH—CO—N(C$_3$H$_7$)$_2$, —NH—CO—N(cyclo-C$_3$H$_5$)$_2$ or —NH—CO—N[CH(CH$_3$)$_2$]$_2$. It is furthermore preferred in this case if $R^3$ represents hydrogen.

In the formulae (IID) and (IIID), R* represents one of the residues $R^6$-$R^{43}$, which can be bonded to a nitrogen atom. In particular, R* represents a linear or branched, saturated or unsaturated acyl group with 1 to 20 carbon atoms which can also contain carbon cycles, heterocycles or aromatic rings in the carbon chain and whose carbon chain can furthermore be substituted with one or more of the residues $R^6$-$R^{43}$.

R in the formulae (IIE) and (IIIE) represents one of the residues $R^6$-$R^{43}$ and preferably an amino group, alkylamino group or dialkylamino group, wherein the alkylgroup or alkyl groups comprise 1 to 20 carbon atoms, wherein the alkyl groups also comprise or contain carbocyclic compounds, heterocyclic compounds and aromatic systems and the alkyl groups can be branched or unbranched and saturated or unsaturated and substituted with one or more of the residues $R^6$-$R^{43}$. Particularly preferred for R are —CH$_2$F, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_3$, —C$_2$H$_5$, —C$_3$H$_7$, —CH(CH$_3$)$_2$, —C(CH$_3$)$_3$, —C$_4$H$_9$, —CH$_2$—CH(CH$_3$)$_2$, —CH(CH$_3$)—C$_2$H$_5$, —C$_5$H$_{11}$, —C$_6$H$_{13}$, —C$_7$H$_{15}$, —C$_8$H$_{17}$, -cyclo-C$_3$H$_5$, -cyclo-C$_4$H$_7$, -cyclo-C$_5$H$_9$, -cyclo-C$_6$H$_{11}$, -Ph, —CH$_2$-Ph, —CPh$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH=C(CH$_3$)$_2$, —C≡CH, —C≡C—CH$_3$ and —CH$_2$—C≡CH.

Particularly preferred are the following compounds of the formula (I): 8-α-ergolines, 8-α-1,6-dimethylergolines, 8-α-1-methylergolines, 8-α-6-methylergolines, 8-α-10-methoxyergolines, lisuride (CAS-No.: 18016-80-3, 3-(9,10-didehydro-6-methylergoline-8alpha-yl)-1,1-diethylurea), d-isolysergic acid, d-isolysergic acid amide, d-isolysergic acid di-ethylamide, proterguride and terguride ((+)-1,1-diethyl-3-(6-methyl-8α-ergolinyl)-urea). Particularly preferred is the use of terguride (trans-dihydrolisuride) and lisuride.

The aforementioned substances and the compounds of the general formulae (I)-(IIIE) are suitable in particular for the prophylaxis and treatment of pulmonary arterial hypertension, of endogenously induced or exogenously induced glomerulosclerosis or secondary Raynaud's phenomenon or syndrome.

That the compounds according to the general formula (I) are suitable for the prophylaxis and treatment of constrictive capillary arteriopathy was surprising because a person skilled in the art had not considered such compounds based on the prior art, since these indications exactly are mentioned as side effects in compounds of the general formula (I) or in 8-α-ergolines. The company Schering AG, for example, mentions in its package insert for the medicament Teluron®, which contains terguride as an 8-α-ergoline, that Raynaud's phenomenon or syndrome, for example, may occur. Moreover, it is known in the literature that ergot alkaloids which also comprise 8-α-ergolines, may cause fibrotic changes. Raynaud's phenomenon, vasospasm, diplopia, retroperitoneal fibrosis, pleural effusions and cardiac valvular fibrosis are known to the person skilled in the art. These negative findings have kept the person skilled in the art from using the compounds of formula (I) for the prophylaxis and treatment of the aforementioned indications.

Thus, a person skilled in the art would not use the compounds according to the general formula (I), and in particular lisuride and terguride, for the prophylaxis and treatment of constrictive capillary arteriopathy characterized by the diseases pulmonary arterial hypertension, endogenously induced or exogenously induced glomeruloscleroses and secondary Raynaud's syndrome. In particular, a person skilled in the art would not at all consider the indications Raynaud's phenomenon or syndrome and pulmonary hypertension because they are explicitly mentioned as side effects for 8-α-ergoline active agents. In particular the mention of such side effects in a package insert for a pharmaceutical from the group of active agents of the 8-α-ergolines concretely suggests to a person skilled in the art that there was an intensive clinical investigation of the active agent. There is thus no cause for a person skilled in the art to doubt the information and statements on a packaging insert of a pharmaceutical.

Postural hypertension is known as a side effect of dopaminergic ergot derivatives including lisuride and terguride. Since the administration of ergolines and ergot derivatives entails stronger gastrointestinal side effects such as, for example, nausea and sicchasia, a therapeutic benefit was partially disputed in principle.

Therefore, it was all the more surprising when it was found that terguride and lisuride have a therapeutic effect and were not, as was to be expected, contra-indicated in the case of the diseases pulmonary arterial hypertension (PAH), endogenously induced or exogenously induced glomerulosclerosis and secondary Raynaud's phenomenon or syndrome, which are herein collectively referred to as constrictive capillary arteriopathy.

Hypertension is the medical term for high blood pressure. The term "blood pressure" refers to the pressure created when blood circulates along the inner vessel wall of the arteries. As a rule, blood pressure is indicated by two quantities, namely arterial pressure, when the heart contracts between the individual heart beats and relaxes again (the systolic and the diastolic pressure).

Blood pressure normally changes in the course of the day and normally increases with age. In addition, physical activities affect blood pressure. Blood pressure increases in response to physical and psychological stress. Patients with hypertension have an increased blood pressure (mostly above 140/90 mm Hg) also in a state of rest. Untreated hypertension leads to the heart and also the arteries being subjected to more stress which can lead to damage to the tissue. In turn, this is a risk factor and may lead to cardiac defects, cardiac infarction (myocardial infarction) and stroke.

In contrast, pulmonary hypertension or glomerulosclerosis for example lead to a local change of vasoreactivity, which leads to a local increase of blood pressure without causing a detectable increase of the systemic blood pressure.

For example, high blood pressure manifests itself in the pulmonary circulation in the case of pulmonary hypertension. In contrast, the blood pressure for example in the arms or in the rest of the body is normal and lower. Thus, pulmonary hypertension is significantly different from (general) hypertension. As a rule, pulmonary hypertension is the result of a disease of the heart and/or the lungs. Pulmonary hypertension is present when the blood pressure in the pulmonary arteries exceeds normal systemic blood pressure, which must be ascribed to local changes of the vasoreactivity and the structure of the small arteries, the so-called arterioles. This leads to stress on the right side of the heart. Pulmonary hypertension is a serious problem. It manifests itself in symptoms like shortness of breath after little exertion, feeling of tiredness, fainting and chest pains. These symptoms usually limit physical exercise and activities.

The difference in aetiology as well as different approaches with regard to the treatment of hypertension (also referred to as essential or general hypertension) and pulmonary hypertension make clear the significant difference between these two diseases. While ACE inhibitors such as, for example, captopril, diuretics such as, for example, furosemide, angiotensin-2 receptor blockers such as, for example, losartan, alpha and beta blockers such as, for example, prazosin and propanolol, direct vasodilators such as, for example minoxidil or centrally active agents such as, for example, clonidine, are used for the treatment of hypertension, none of these active substances is suitable for the treatment for pulmonary hypertension, nor are they used for this purpose.

Therefore, no positive effect on hypertension can be derived from a positive effect of terguride or lisuride on pulmonary arterial hypertension, or vice versa.

Furthermore, the present invention relates to pharmaceutical compositions prepared using at least one compound according to formula (I) or a salt thereof, and in particular using lisuride or terguride.

These pharmaceutical compositions contain at least one compound of the general formula (I) and in particular lisuride or terguride in a concentration of active substances of 0.1 to 10 mg per single dose together with at least one pharmacologically compatible carrier, auxiliary substance or solvent.

The pharmaceutical compositions are preferably provided as tablets, layered tablets, pills, capsules, microcapsules, retard-oral medicines, transdermal systems, suppositories, micro-formulations, nano-formulations, liposomal formulations, drops, nose drops, nose sprays, aerosols, ampoules, solutions, emulsions, dispersions, powders, inhalation powders, micro-crystalline formulations or inhalation sprays and are suitable for, in particular, oral, sublingual, parenteral, cutaneous, buccal, percutaneous, inhalative or nasal administration.

Lactose, starch, sorbitol, sucrose, cellulose, magnesium stearate, dicalcium phosphate, calcium sulphate, talcum, mannitol, ethyl alcohol and the like can be used as pharmacologically compatible carrier. Powder as well as tablets can consist of 5% to 95% of such a carrier.

Moreover, starch, gelatine, natural sugars, both natural as well as synthetic rubbers such as, for example, acacia gum or guar gum, sodium alginate, carboxymethyl cellulose, polyethyleneglycol and waxes can be used as binding agents. Boric acid, sodium benzoate, sodium acetate, sodium chloride and the like can serve as lubricants.

Furthermore, disintegrating agents, coloring agents, flavoring agents and/or binding agents can be added to the pharmaceutical compositions.

Liquid formulations include solutions, suspensions, sprays and emulsions. For example, injection solutions based on water or water-propylene glycol for parenteral injections.

Low-melting waxes, fatty acid esters and glycerides are preferably used for preparing suppositories.

Capsules are produced, for example, from methylcellulose, polyvinyl alcohols or denaturated gelatine or starch.

Starch, sodium carboxymethyl starch, natural and synthetic rubbers such as carob gum, karaya, tragacanth and agar as well as cellulose derivatives such as methylcellulose, sodium carboxymethylcellulose, micro-crystalline cellulose as well as alginates, aluminas and bentonites can be used as disintegrating agents. These constituents can be used in quantities of 2% to 30%.

Sugar, starch from grain, rice or potatoes, natural rubbers such as acacia gum, gelatine, tragacanth, alginic acid, sodium alginate, ammonium calcium alginate, methylcellulose, sodium carboxymethylcellulose, hydroxypropyl methylcellulose, polyvinylpyrrolidone as well as inorganic compounds such as magnesium aluminum silicates can be added as binding agents. The binding agents can be added in quantities of 1 to 30% by weight.

Stearates such as magnesium stearate, calcium stearate, potassium stearate, stearic acid, high-melting waxes and water-soluble lubricants such as sodium chloride, sodium benzoate, sodium acetate, sodium oleate, polyethylene glycol and amino acids such as leucine can be used as lubricants. Such lubricants can be used in quantities of 0.05 to 15% by weight.

Subcutaneous formulations and transdermal systems must be mentioned as further preferred formulations. Such subcutaneous formulations and transdermal systems preferably consist of a matrix, in particular a biodegradable polymer matrix in which the at least one compound according to formula (I), preferably lisuride or terguride, is incorporated. Preferably, biodegradable polymers are used for creating this matrix.

The following can be mentioned as examples for biodegradable polymers: polyvalerolactones, poly-ϵ-decalactones, polylactides, polyglycolides, copolymers of the polylactides and polyglycolides, poly-ϵ-caprolactone, polyhydroxybutyric acid, polyhydroxybutyrates, polyhydroxyvalerates, polyhydroxybutyrate-co-valerates, poly(1,4-dioxane-2,3-diones), poly(1,3-dioxane-2-ones), poly-para-dioxanones, polyanhydrides such as polymaleic acid anhydrides, polyhydroxymethacrylates, fibrin, polycyanoacrylates, polycaprolactonedimethylacrylates, poly-b-maleic acid, polycaprolactonebutyl-acrylates, multiblock polymers such as from, for example, oligocaprolactonedioles and oligodioxanonedioles, polyetherester multiblock polymers such as, for example PEG and poly(butylenterephtalate. Polypivotolactones, polyglycol acid trimethyl-carbonates, polycaprolactone glycolides, poly(g-ethylglutamate), poly(DTH-iminocarbonate), poly(DTE-co-DT-carbonate), poly(bisphenol A-iminocarbonate), polyorthoester, polyglycol acid trimethyl-carbonates, polytrimethylcarbonates, polyiminocarbonates, poly(N-vinyl)-pyrrolidone, polyvinyl alcohols, polyesteramides, glycolated polyester, polyphosphoesters, polyphosphazenes, poly[p-carboxyphenoxy)propane] polyhydroxypentane acid, polyanhydrides, polyethylene oxide-propylene oxide, soft polyurethanes, polyurethanes with amino acid residues in the backbone, polyetheresters such as polyethylene oxide, polyalkene oxalates, polyorthoester as well as their copolymers, carrageenanes, fibrinogen, starch, collagen, protein-based polymers, polyamino acids, synthetic polyamino acids, zein, modified zein, polyhydroxyalkanoates, pectic acid, actinic acid, modified and non-modified fibrin and casein, carboxymethylsulfate, albumin, furthermore hyaluronic acid, heparansulphates, heparin, chondroitinesulphate, dextran, b-cyclodextrines, copolymers with PEG and polypropyleneglycol, gum arabic, guar, gelatine, collagen, collagen-N-hydroxysuccinimide, modifications and copolymers and/or mixtures of these substances.

Biological polymers are preferred, such as starch and denaturated starch, cellulose, glycosaminoglycans and collagen as well as semi-synthetic and synthetic polymers such as silicones, silicone elastomers, polydimethylsiloxane, polydimethylsiloxane containing siliciumdioxide, polydimethylsiloxane containing polyalkylene oxide (Gelest®), polytetrafluoroethylene (Teflon®), polylactides, polyglycolides, polyethylene glycol, polylactid-polyglycolide-co-polymers, polyanhydrides, ethylenevinylacetate-polymers, poly(methylmethacrylate), celluloseethylether, poly(ethylacrylate), poly(trimethylammoniumethyl-methacrylates), polydimethylsiloxanes, hydroxyethyl-polymethacrylates, polyurethanes and polystyrene-butadiene-copolymers.

Moreover, such transdermal systems can also consist of microspheric particles or nanoparticles or microcrystals, which contain at least one compound according to the general formula (I). Additionally, such particles can be introduced into a gel and applied in this form.

Moreover, the use of microparticles of biocompatible ceramics such as hydroxyapatite is also possible to which the compounds according to formular (I) are attached or into which they are incorporated.

DESCRIPTION OF THE FIGURES

FIG. 4 shows the influence of serotonin and terguride on the expression of Col1 A2 in smooth muscle cells from pulmonary arteries.

EXAMPLES

Example 1

Antiproliferative Action

Human pulmonary smooth muscle cells (PromoCell) were cultivated up to confluence in six-well plates in a PromoCell culture medium in accordance with the manufacturer's specifications. The pulmonary smooth muscle cells were then seeded in 24-well plates PromoCell culture medium in a cell density of $5 \times 10^4$ cells per well. After adhesion of the cells had taken place, the culture medium was replaced and an arrest of growth was effected by cultivation in a medium with 0.2% fetal calf serum over the course of 48 hours.

Figure 1:
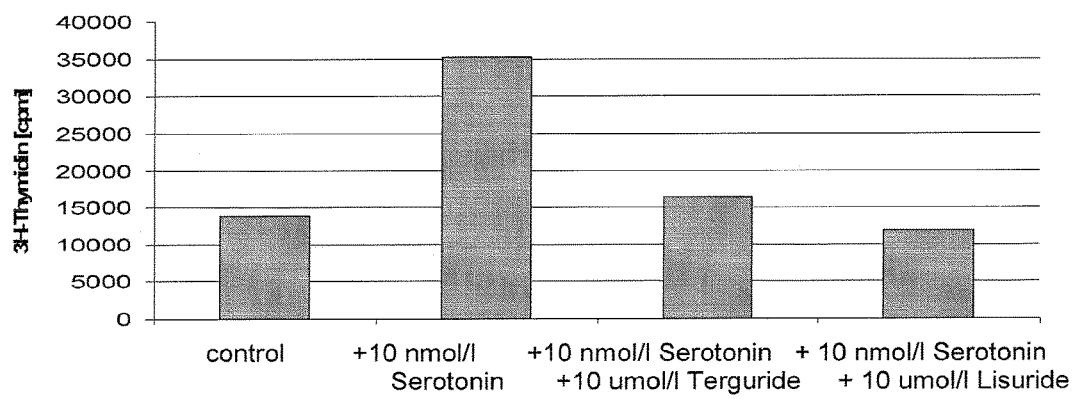
FIG. 1 shows that, in the presence of increased serotonin concentrations, serotonin as a growth factor leads to a proliferation of smooth muscle cells. In the presence of a compound according to the general formula (I), such as lisuride or terguride, this cell proliferation is significantly reduced by the antagonistic action of these substances (on serotonin 5-HT2 receptors). From this in-vitro model, it can be deduced that, given conditions that lead to an increased serotonin released locally or systemically, the above-mentioned substances can inhibit an exuberant proliferation of smooth muscle cells in blood vessels during the healing process.
Figure 2:
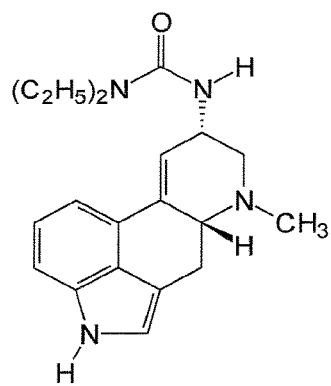
FIG. 2 shows the chemical structure of lisuride.
Figure 3:
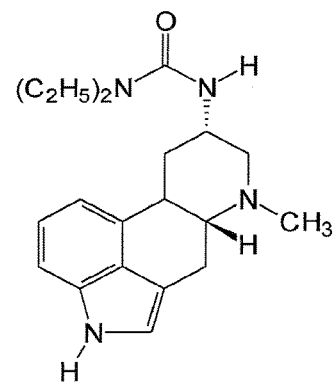
FIG. 3 shows the chemical structure of terguride.

In order to examine the antiproliferative effect of the substance, the cells were first preincubated with 10 μmol/l of active agents. The growth behavior of the cells was then stimulated with serotonin ($10^{-8}$ mol/l). For measuring cell proliferation. [3H]thymidine (Amersham) was added to the cultures and incubated for 24 hours. First, the cells were then incubated twice in ice-cold phophate buffered saline solution and then, in ice-cold 10% trichloroacetic acid for 30 minutes at 4° C. The cells were then dissolved in 0.1 molar sodium hydroxide solution (0.5 ml/well). After neutralization with acetic acid, the incorporation of [3h]-thymidine was determined by liquid scintillation measurements. The determinations were performed in triplicate. The average is shown in each case in FIG. 1.

Example 2

Preparation of a Formulation for Oral Application with Terguride 25.0 g terguride, micronized, is mixed in a tumbling mixer for 5 minutes at, for example, 162 rpm with 4035.0 g lactose, 1800.0 microcrystalline cellulose and 120.0 g croscarmellose Na after prior sieving of the auxiliary agents. This pre-mixture is then poured over a sieve having 0.8 mm mesh size. 20.0 g magnesium stearate is added and mixing is again carried out for 1 minute. The press body thus obtained is pressed on a suitable tablet press (e.g. rotary press) to form 50,000 tablets (theoretical yield) having a diameter of 7 mm and a tablet weight of 120 mg, corresponding to a dose of 0.5 mg terguride/tablet. The tablets thus produced release the active agent after being introduced into water quickly, and, after max. 60 minutes, nearly completely.

Example 3

Preparation of a Formulation for Oral Application of Lisuride with Retarded Release 2.0 g lisuride hydrogenmaleate, micronized, is mixed in a tumbling mixer for 5 minutes at, for example, 180 rpm with 750.0 g hydroxyethylcellulose (tylose H) and 243.0 g microcrystalline cellulose after prior sieving of the auxiliary agents. This pre-mixture is then poured over a sieve having 0.8 mm mesh size. 5.0 g magnesium stearate is added and mixing is again carried out for 1 minute. The press body thus obtained is pressed on a suitable tablet press (e.g. rotary press) to form 10,000 tablets (theoretical yield) having a diameter of 6 mm and a tablet weight of 100 mg, corresponding to a dose of 0.2 mg lisuride hydrogenmaleate/tablet. The tablets thus produced release the active agent after being introduced into water in a retarded manner, so that 60-70% of the dose from the formulation was released after approx. 2 h.

Example 4

Preparation of a Sterile Lyophilisate with Lisuride Hydrogenmaleate for Injection after Dissolution 2.0 g lisuride hydrogenmaleate is dissolved together with 20.0 g lactose monohydrate, 0.4 g citric acid monohydrate and 1.0 g sodium citrate dihydrate in 976.6 water for injection purposes. The colorless to slightly yellowish solution obtained has a pH value of between 4.5 and 5.4. This solution is pre-filtered through a membrane filter and then filtered sterilely under aseptic conditions through another membrane filter (0.2 µm). 1.0 g, respectively, of the solution thus obtained is filled into sterilized vials having a filling volume of 6 ml, provided with a rubber stopper suitable for the subsequent freeze-drying process, and frozen at −40° C. to −50° C. in a lyophilizer. Then, a drying or after drying process is carried out in a vacuum, obtaining a dried substance cake. These vials are sealed and crimped in aseptic conditions. In this way, 1000 vials (theoretical yield) with 2 mg, respectively, of lyophilized lisuride hydrogenmaleate are produced. The lyophilisate is reconstituted by being dissolved out with sterile physiological saline solution and yields a ready-for-use sterile solution for injections or infusion for immediate application.

Example 5

Preparation of a Matrix Plaster with Terguride for Transdermal Application 2.5 g terguride is added to 2.13 g acetone and 51.54 g of a solution of alkali butyl methacrylate copolymer (Eudragit 100 solution). 5.0 polyvinyl pyrrolidones (Povidone 25), 2.5 g propyleneglycol, 5.0 g dodecyl-N,N-dimethylaminoacetate (alternatively, 5.0 g 1-dodecanol), 1.0 g Foral E 105 and 0.65 g of an antioxidant (e.g. butylhydroxyanisole) are added to the solution. The coating solution thus obtained is continuously spread onto a polymer sheet of polyethylene under suitable process conditions in a coater and then dried to form a basis weight of 50 mg/10 cm$^2$ (±5%) of coated surface. The sticky matrix thus obtained is laminated with a polymer sheet siliconized on one side and, in a further step, punch-cut to form plasters in a size suitable for therapeutic application (e.g. 20 cm$^2$) and packaged in aluminum sachets. The terguride plaster thus produced releases the active agent continuously over several days with a rate of between 0.1 to 0.5 µg/cm$^2$/h to the systemic circulation after application onto intact hairless skin.

Example 6

Preparation of a Membrane Plaster with Lisuride for Transdermal Application

Using a laboratory coater, a membrane of micro-porous polyethylene (Solupor® 10P05A), as a control membrane (or, alternatively, of ethylene vinylacetate copolymer (EVA, Cotran® 3M 9728)), is coated with a skin-compatible silicon adhesive (BioPSA®7-4202) (alternatively, polyisobutylene adhesive, Oppanol®) and dried with a basis weight of approx. 10 to 25 mg/cm$^2$ and then laminated with a release liner (polyethylene) siliconized on one side.

In a suitable sealing machine, the laminate thus obtained is sealed in a ring shape with heat-sealable polyethylene except for a small opening and punched. Approx. 0.5 ml of a 1% solution of lisuride in 2-propanol, hydroxypropyl cellulose (Klucel® LF) and tocopherol is introduced by means of a suitable injecting device via the remaining opening into the cavity created and then sealed completely.

After equilibrating and pulling off the release liner the membrane plaster can be adhered to the intact hairless skin and releases lisuride constantly and at a constant rate. The dosage can be set by the varying plaster size.

Example 7

Preparation of a Sterile Formulation with Terguride to be Applied Subcutaneously 50 g micronized terguride is homogeneously mixed with 50 g polydimethylsiloxane and shaped to form a strand-shaped core matrix by standard methods, preferably by extrusion. The strand is cut into portions of 30 mm. A core extrudate free of active agents and having identical dimensions is produced according to the same process. In a second step, tube-shaped membranes having a wall thickness of, for example, 0.2 mm wall thickness are produced from commercially available polydimethylsiloxane containing siliciumdioxide or, for example, polydimethylsiloxane containing Pt-catalyzed crosslinked polyalkylene oxide (Gelest®). The membranes are cut in lengths of 60 mm and left to swell in cyclohexane. Then, the active agent-containing core matrix is inserted and the extrudate which is free of active agent is inserted from both sides of the tubular membrane, for example such that an air-filled space of approx. 1-3 mm is created on both sides between the active agent-containing core and the extrudate free of active agent. Then, cyclohexane is removed by evaporation, the formulation is cut to a total length of 50 mm, so that a closure is created on both sides of the formulation by core material free of active agent. The formulation is gas-sterilized by a standard method (ethyleneoxide, $H_2O_2$). The position of the formulation at the place of application can be detected at any time by ultrasound detection due to the enclosed air.

Example 8

Pulmonary Hypertension

Description of the Experiment 1 monocrotaline (60 mg/kg; Sigma) was administered to rats on the day of the experiment. For this purpose, the substance was dissolved in 0.5 molar hydrochloric acid and the pH value was then adjusted to 7.4 with 0.5 molar sodium hydroxide solution. The solution was administered to male Sprague-Dawley rats as a single subcutaneous injection in a dose of 60 mg/kg. The same volume of isotonic saline solution was administered to control animals.

On days 14-28 of the experiment, either 0.25 mg/kg lisuride or 2.5 mg/kg terguride was administered daily by means of an oesophageal tube to groups of 6 animals, respectively, which were treated with monocrotaline on day 1. The dosage specifications in this case relate to the free base of the substances. The substances were used as hydrogenmaleate salt or free base. They were introduced into distilled water in the presence of traces of ascorbic acid and administered by oesophageal tube in the morning and in the evening in a volume of 2 mL. The same quantity of water was administered to control animals.

On day 28 of the experiment, 2 hours after the last administration of the substance, the animals were put under general anesthesia using pentobarbital. Then, a tracheostomy was performed on the animals and the animals were respirated at 10 ml/kg and a frequency of 60 s$^{-1}$ (SAR830A/P; IITC). Anesthesia was maintained by inhalation of isoflurane.

The mean arterial pressure and the right ventricular systolic blood pressure were determined. The systemic arterial pressure was measured using a Millar catheter in the left carotid artery. A millar catheter with a pressure sensor (Millar Instruments, model SPR-534) was inserted through the right jugular vein and pushed up to the right ventricle of the heart and used for measuring the right ventricular pressure (RVSP). The signal was amplified by means of a HSE coupler Series 500 and supplied to a registration unit for evaluation.

After the pressure measurements had been performed, the rats were perfused with physiological saline solution. The right lung was removed, deep-frozen and processed for determining the collagen content. To this end, the tissue was first homogenized and analyzed, drawing on the method by Berg (Meths Enzymol. 82, 372 (1982)). First a hydrolysis of the sample was carried out in 6 molar hydrochloric acid for 16 hours at 116° C. Hydroxyproline was subsequently oxidized to pyrrole followed by a complexation with p-dimethylamino benzaldehyde. The color complex created was measured photometrically at 560 nm and the hydroxprolin content of the samples was determined by means of a calibration curve. The results are given as µg/g protein in the lung tissue.

Results:
   a) Influence of the treatment with lisuride or terguride on day 15-28 of the experiment on the systolic pressure in the right ventricle (RVPsys) and the systematic arterial pressure (SAP)

|  | RVPsys [mmHg] | SAP [mmHg] |
|---|---|---|
| Control | 23 ± 4 | 118 ± 5 |
| Monocrotaline | 55 ± 5 | 114 ± 7 |
| Monocrotaline + 0.25 mg/kg Lisuride bid | 43 ± 7 | 109 ± 9 |
| Monocrotaline + 2.5 mg/kg Terguride bid | 39 ± 3 | 111 ± 7 |

Results are averages±SEM (N=6)
   b) Influence of the treatment with lisuride and terguride on the day 15-28 of the experiment on the hydroxyproline content of the lung

|  | Hydroxyproline [ug/g protein] |
|---|---|
| Control | 1.2 ± 0.2 |
| Monocrotaline | 4.2 ± 1.1 |
| Monocrotaline + 0.25 mg/kg Lisuride bid | 3.3 ± 0.8 |
| Monocrotaline + 2.5 mg/kg Terguride bid | 2.7 ± 1.2 |

Results are averages±SEM (N=6)

Evaluation of the Experiment

Endothelial damage of the lung, which entails an exuberant production of connective tissue and the development of pulmonary hypertension, occurs in rats after administration of monocrotaline. Collagen accumulation, measured as hydroproline content in the lung tissue, and the increase in systolic pressure in the right ventricle reflect these structural and functional changes. Possible therapeutic effects of a treatment with lisuride or terguride were examined in this model for pulmonary hypertension. Under the conditions of the experiment, therapy was not initiated at the time of the monocrotaline treatment, that is, not at the time of the occurence of the damage, but not until 14 days later. At this point in time, extensive changes to the vessels and an increase in pressure have manifested themselves according to literature. Therapy with lisuride or terguride reduces the increase in pressure in the right ventricle as an indirect measure for pulmonary hypertension in the sense of a therapeutically desirable effect.

As a structural correlate, a decrease of the hydroxyproline content increased by the monocrotaline in the sense of a "reverse remodelling" was observed during the therapy with the two substances. In this established animal model, lisuride and terguride have qualities of efficiency which make therapeutic use on patients with pulmonary hypertension successful.

The experimental example described demonstrates the successful use of the ergolines for the treatment of pulmonary hypertension by the example of lisuride and terguride.

Example 9

Pulmonary Hypertension

Description of the Experiment 1 monocrotaline (60 mg/kg; Sigma) was administered to rats on the day of the experiment. For this purpose, the substance was dissolved in 0.5 molar hydrochloric acid and the pH value was then adjusted to 7.4 with 0.5 molar sodium hydroxide solution. The solution was administered to male Sprague-Dawley rats as a single subcutaneous injection in a dose of 60 mg/kg. The same volume of isotonic saline solution was administered to control animals.

Induction of pulmonary arterial hypertension

On days 1-28 of the experiment, either 1.2 mg/kg terguride was administered intraperitoneally twice daily to groups of 4 animals, respectively, which were treated with monocrotaline on day 1. Terguride was introduced into distilled water in the presence of traces of ascorbic acid and administered by oesophageal tube in the morning and in the evening in a volume of 2 mL. The same quantity of physiological saline solution was administered to control animals.

On day 28 of the experiment, 2 hours after the last administration of the substance, the animals were put under general anesthesia using pentobarbital. Then, a tracheostomy was performed on the animals and the animals were respirated at 10 ml/kg and a frequency of 60 $s^{-1}$ (SAR830A/P; IITC). Anesthesia was maintained by inhalation of isoflurane.

Determination von right ventricular systolic pressure (RVSP) and SAP (systolic arterial pressure)

The mean arterial pressure and the right ventricular systolic blood pressure were determined. The systemic arterial pressure was measured using a Millar catheter in the left carotid artery. A millar catheter with a pressure sensor (Millar Instruments, model SPR-534) was inserted through the right jugular vein and pushed up to the right ventricle of the heart and used for measuring the right ventricular pressure (RVSP). The signal was amplified by means of a HSE coupler Series 500 and supplied to a registration unit for evaluation.

Determination of right ventricular hypertrophy

After the pressure measurements had been performed, the rats were perfused with physiological saline solution. The heart was removed and prepared by dissection of the right ventricle, the septum as well as the left ventricle of each heart. The tissue preparations were freeze-dried and the dry weights were then determined by weighing out. For each individual animal, the quotient: weight of the right ventricle/ weight of the left ventricle and septum (RV/LV+S) was determined from these animals as a measure for right ventricular hypertrophy.

Determination of the musculization or arterial capillary vessels of the lung

The lungs were removed, fixated in formalin and embedded in paraffin. Paraffin sections were obtained and an immunohistochemical double staining was carried out according to standard protocols. Smooth muscle cells of the vessels were stained with an antibody against actin and the endothelium was stained by means of antibodies against von Willebrand factor. For evaluation purposes, ≥80 intracinous arteries having a diameter >50 μm were used. The vessels were subdivided into 3 categories: non-muscularized vessels with 20%, partially muscularized vessels with >20%, but <70%, and fully muscularized vessels with >70% lining of the cross-section of the vessel with smooth muscle cells.

Results:

a) Influence of the treatment with terguride on days 1-28 of the experiment on the systolic pressure in the right ventricle (RVSP) and the systematic arterial pressure (SAP)

|  | RVSP [mmHg] | SAP [mmHg] |
| --- | --- | --- |
| Control | 31.0 ± 3.6 | 104.0 ± 13.3 |
| Monocrotaline | 64.4 ± 14.5 | 93.7 ± 19.4 |
| Monocrotaline + 0.4 mg/kg Terguride bid | 36.4 ± 3.6 | 97.5 ± 15.2 |

Results are averages±SD (N=4)

b) Influence of the treatment with terguride on days 1-28 of the experiment on right ventricular hypertrophy, measured as ratio: weight of right ventricle vs. weight of left ventricle and septum

|  | RV/LV + S |
| --- | --- |
| Control | 0.31 ± 0.06 |
| Monocrotaline | 0.74 ± 0.14 |
| Monocrotaline + 0.4 mg/kg Terguride bid | 0.33 ± 0.08 |

Results are averages±SD (N=4)

c) Influence of the treatment with terguride on days 1-28 of the experiment on the muscularization of arterial capillary vessels (20-50 μm diameter) in the lung

|  | Proportion of non-muscularized vessel [%] | Proportion of partially muscularized vessel [%] | Proportion of fully muscularized vessel [%] |
| --- | --- | --- | --- |
| Control | 57.8 ± 14.6 | 3.2 ± 2.3 | 14.8 ± 6.2 |
| Monocrotaline | 40.4 ± 16.0 | 42.3 ± 4.4 | 64.0 ± 7.7 |
| Monocrotaline + 0.4 mg/kg Terguride bid | 1.9 ± 1.6 | 57.8 ± 14.6 | 21.3 ± 12.6 |

Results are averages±SD (N=4)

Evaluation of the Experiment

Endothelial damage of the lung, which entails an exuberant proliferation of smooth muscle cells in arterial capillary vessels of the lung and the development of pulmonary hypertension, occurs in rats after administration of monocrotaline. The increase in systolic pressure in the right ventricle at constant systemic blood pressure as well as right ventricular hypertrophy reflect these structural and functional changes.

Possible therapeutic effects of a treatment with terguride were examined in this model for pulmonary hypertension. Under the conditions of the experiment, therapy was initiated immediately after monocrotaline administration. During therapy with terguride, the increase in pressure in the right ventricle as an indirect measure for pulmonary hypertension is almost always suppressed. Under the conditions of the experiment, the systemic blood pressure is not changed in a detectable way.

A complete suppression of the monocrotaline-induced right ventricular hypertrophy also occurs during therapy. As a therapeutic effect, a decrease of monocrotaline-induced muscularization of arterial capillary vessels was observed during therapy. In this established animal model, terguride has qualities of efficiency for pulmonary hypertension in all relevant functional and structural parameters which make therapeutic use on patients with pulmonary hypertension successful.

Example 10

Inhibition of the expression con Col IA2 in smooth muscle cells of the pulmonary arteries A possible stimulating influence of serotonin on the expression of Col A2 as well as the inhibitory action of terguride was investigated in the experiment. The investigations were performed on humal pulmonary smooth musclecells (Cambrex). The cells were cultivated in CC-3182 medium (Cambrex) according to the manufacturers specifications. 5% of serotonin-depleted fetal calf serum (FCS) (HyClone) pretreated with activated carbon were added.

Upon obtaining a confluent cell lawn, the cells were cultivated for another 2 days in 5% FCS. A medium with the addition of 0.5% FCS was used for the experiment. The cells were cultivated further for 48 hours after the addition of serotonin (100 nmol/L) and/or terguride (100 nmol(L). The incubations were performed in triplicates.

The total RNA was obtained unsing the Rneas Kit (Qiagen) in accordance with the manufacturer's specifications. Reverse transcription into cDNA was effected by means of oligo-dT Primer (Roche).

Then, gene expression was quantified by means of SYBR Green real-time PCR on an ABI Prism 7700 Sequence Detection System (Applied Biosystems, Foster City, Calif., USA) in accordance with standard protocols. The forward primer 5'-GGTCAGCACCA-CCGATGTC-3'(SEQ ID NO: 1) and the reverse primer 5'-CACGCCTG-CCCTTCCTT-3' (SEQ ID NO: 2) were used as specific primer pair for human Col1 A2 in the PCR analysis.

For standardization of differences in the total quantity of RNA in individual samples, the expression of Col1 A2 was normalized to the expression of the enzyme glycerinaldehyde-3-phosphate dehydrogenase (GAPDH) which is expressed constitutively in the cells. For this purpose, the following primers were used: forward primer 5'-CAATGC-CTCCTGCACCACCAAC-3 ,' (SEQ ID NO: 3) and reverse primer: AGGGGCCATCCACAGTCTTCT-3' (SEQ ID NO: 4).

The expression performance of Col1 A2 and GAPDH in individual samples was determined using standard evaluation methods and quantified as Col1A2/GAPDH ratios.

The results were represented as "box and whisker" plots.

As is apparent from the illustration, expression of Col A2 in human smooth muscle cells from pulmonary arteries is significantly stimulated in the presence of 100 nmol/L serotonin as compared with a control batch. This suggests a trophical action by serotonin. An exuberant deposition of collagen, together with the proliferation of smooth muscle cells, contributes to the pathophysiology of pulmonary arterial high pressure.

Expression of Col1 A2 is inhibited in the presence of terguride, with the inhibitory action being more pronounced in the presence of serotonin. Therefore, a possible therapeutic benefit of terguride in the treatment of patients with pulmonary hypertension can be deduced from the qualities of efficiency described herein.

The invention claimed is:

1. A method for the treatment of constrictive capillary arteriopathy, which is endogenously induced or exogenously induced glomerulosclerosis or secondary Raynaud's syndrome comprising administering to a subject in need thereof an effective amount of a compound of formula (I)

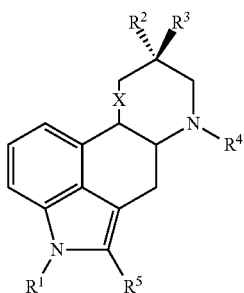

(I)

wherein
R$^1$ represents H, —CH$_3$, —C$_2$H$_5$, —C$_3$H$_7$, —CH(CH$_3$)$_2$ or —CH$_2$—CH=CH$_2$;
R$^2$ represents —NH—CO—N(CH$_2$CH$_3$)$_2$;
R$^3$ represents H;
R$^4$ represents —CH$_3$, —C$_2$H$_5$, —C$_3$H$_7$, —CH(CH$_3$)$_2$, -cyclo-C$_3$H$_5$ or —CH$_2$—CH=CH$_2$;
R$^5$ represents —H, —F, —Cl, —Br or —I; and
X represents a single bond or double bond;
or a salt, enantiomer, mixture of enantiomers, diastereomer, mixture of diastereomers, hydrate, solvate or racemate thereof.

2. A method according to claim 1, wherein the compound of formula (I) is lisuride.

3. A method according to claim 1, wherein the compound of formula (I) is in a pharmaceutical composition which comprises said compound of formula (I) in a concentration of active substances of 0.1 to 10 mg per single dose together with one or more pharmacologically compatible carriers, auxiliary substances and/or solvents.

4. A method according to claim 3, wherein the pharmaceutical composition is suitable for oral, sublingual, parenteral, cutaneous, buccal, percutaneous or subcutaneous administration.

5. A method according to claim 3, wherein the pharmaceutical composition is provided in a form selected from the group consisting of tablets, layered tablets, capsules, retard-oral medicines, suppositories, micro-formulations, nano-formulations, liposomal formulations, drops, ampoules, solutions, emulsions, dispersions, powders, micro-crystalline formulations and subcutaneous formulations.

6. A method according to claim 1, wherein the compound of formula (I) is terguride.

7. A method for the treatment of constrictive capillary arteriopathy, which is endogenously induced or exogenously induced glomerulosclerosis or secondary Raynaud's syndrome, comprising administering to a subject in need thereof an effective, amount of a compound of formula (I)

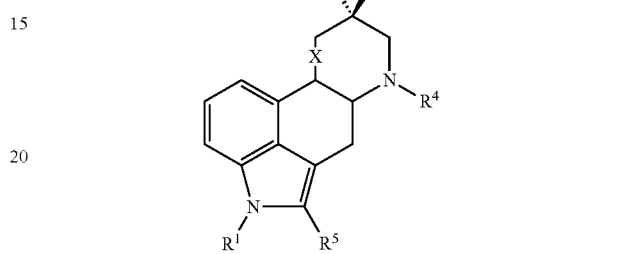

(I)

wherein
R$^1$ represents H, —CH$_3$, —C$_2$H$_5$, —C$_3$H$_7$, —CH(CH$_3$)$_2$ or —CH$_2$—CH=CH$_2$;
R$^2$ represents —NH—CO—N(CH$_2$CH$_3$)$_2$;
R$^3$ represents H;
R$^4$ represents —CH$_3$, —C$_2$H$_5$, —C$_3$H$_7$, —CH(CH$_3$)$_2$, -cyclo-C$_3$H$_7$ or —CH$_2$—CH=CH$_2$;
R$^5$ represents —H, —F, —Cl, —Br or —I; and
X represents a single bond or double bond;
or a salt, enantiomer, mixture of enantiomers, diastereomer, mixture of diastereomers, hydrate, solvate or racemate thereof.

8. A method according to claim 7, wherein the compound of formula (I) is lisuride or terguride.

9. A method according to claim 1, wherein the compound of formula (I) or a pharmaceutically acceptable salt thereof is administered.

10. A method according to claim 3, wherein the pharmaceutical composition is suitable for oral, sublingual or buccal administration.

11. A method according to claim 3, wherein the pharmaceutical composition is provided in a form selected from the group consisting of tablets, layered tablets, capsules, retard-oral medicines, suppositories and ampoules.

* * * * *

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggtcagcacc accgatgtc                                                    19

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cacgcctgcc cttcctt                                                      17

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caatgcctcc tgcaccacca ac                                                22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4 agggggccatc cacagtcttc t                                                21